(12) United States Patent
Gresham

(10) Patent No.: US 7,691,089 B2
(45) Date of Patent: Apr. 6, 2010

(54) ADJUSTABLE TROCAR WASHER

(75) Inventor: Richard D. Gresham, Guilford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 1083 days.

(21) Appl. No.: 11/158,155

(22) Filed: Jun. 21, 2005

(65) Prior Publication Data

US 2007/0005086 A1 Jan. 4, 2007

(51) Int. Cl.
*A61M 5/32* (2006.01)

(52) U.S. Cl. ............................ 604/174

(58) Field of Classification Search ............ 604/540, 604/164.12, 174, 107; 24/9, 11, 15, 17, 616, 24/271, 33, 272, 68 J, 574.1, 19; 411/10, 411/539, 540, 541, 277, 62, 71, 80.5; 606/74; 292/256, 256.6, 256.65, 256.73, 256.75; 424/9.8; 119/821

See application file for complete search history.

(56) References Cited

U.S. PATENT DOCUMENTS

| | | | |
|---|---|---|---|
| 1,579,719 A * | 4/1926 | Lavender | 24/272 |
| 5,002,557 A | 3/1991 | Hasson | |
| 5,073,169 A * | 12/1991 | Raiken | 604/180 |
| 5,122,122 A | 6/1992 | Allgood | |
| 5,147,316 A | 9/1992 | Castillenti | |
| 5,176,697 A | 1/1993 | Hasson et al. | |
| 5,203,773 A | 4/1993 | Green | |
| 5,232,451 A | 8/1993 | Freitas et al. | |
| 5,267,970 A * | 12/1993 | Chin et al. | 604/175 |
| 5,279,564 A | 1/1994 | Taylor | |
| 5,279,575 A | 1/1994 | Sugarbaker | |
| 5,290,249 A | 3/1994 | Foster et al. | |
| 5,330,497 A | 7/1994 | Freitas et al. | |
| 5,354,283 A * | 10/1994 | Bark et al. | 604/180 |
| 5,782,813 A | 7/1998 | Yoon | |
| 5,836,913 A | 11/1998 | Orth et al. | |
| 5,857,999 A | 1/1999 | Quick et al. | |
| 6,432,085 B1 | 8/2002 | Stellon et al. | |
| 6,620,129 B2 | 9/2003 | Stecker et al. | |
| 6,908,454 B2 | 6/2005 | McFarlane | |

FOREIGN PATENT DOCUMENTS

| WO | WO 02/096307 | * 12/2002 |
|---|---|---|
| WO | WO 02096307 A2 | * 12/2002 |

\* cited by examiner

*Primary Examiner*—Nicholas D Lucchesi
*Assistant Examiner*—Diva Ranade

(57) ABSTRACT

An adjustable trocar washer is provided to facilitate sealing an incision in skin. The adjustable trocar washer is configured for use with a trocar or cannula assembly. The adjustable trocar washer generally includes a compressible collar and a skirt formed at the distal end of the compressible collar for sealing an incision in skin. The compressible collar is longitudinally movable along an elongate tubular member associated with the trocar or cannula assembly. A latch mechanism is provided on the compressible collar to secure the collar in a compressed condition about the elongate tubular member.

18 Claims, 6 Drawing Sheets

ADJUSTABLE TROCAR WASHER

BACKGROUND

1. Technical Field

The present disclosure relates to an adjustable trocar washer for use with a cannula or trocar assembly. More particularly, the present disclosure relates, to an adjustable trocar washer having a compressable collar for securing about a cannula and a skirt for sealing an external surface of an abdominal incision.

2. Background of Related Art

During laparoscopic or endoscopic surgical procedures it is necessary to provide sealed access ports into the body cavity. These devices are known as trocars or cannulas. A typical cannula includes an elongate tubular member for providing access into the body cavity through an abdominal incision and a cannula housing having a valve member to seal the elongate tubular member. In order to prevent inadvertent removal or insertion of the elongate tubular member through an abdominal incision, an anchor member is typically provided at a distal end of the elongate tubular member to seal it against an inner surface of the abdominal incision. A securing mechanism is often provided and is movably mounted along the elongate tubular member to seal against an outer surface of the abdominal incision.

One known type of cannula includes a compressible foam collar which is slidably mounted along the elongate tubular member to seal against the outer surface of the abdominal incision. However, the compressible foam collar provides limited vertical stability to the cannula relative to the abdominal wall. Therefore, it is desirable to have a securing mechanism which can seal the outer surface of an abominable incision and also provide substantial vertical stability to the cannula.

SUMMARY

The presently disclosed adjustable trocar washer is provided for use with an elongate tubular member or "cannula" to seal against an outer surface of an abominable incision. The adjustable trocar washer generally includes a collar slidable along the elongate tubular member and a skirt positioned at the distal end of the collar. The collar and skirt are slit along their longitudinal lengths to be adjustably compressible about the elongate tubular member. A latch mechanism is provided on the collar to retain the collar in a compressed condition about the elongate tubular member. In one embodiment, the latch mechanism includes a post provided on one side of the collar slit and a pivotally mounted latch member formed on the opposing side of the collar slit. The latch member may include one or more openings engageable with the post.

The skirt has sufficient flexibility to seal about an incision in the skin. However, the skirt also has sufficient stiffness to provide vertical stability to the cannula. A proximal opening in the skirt is secured to a reduced diameter portion at the distal end of the collar:

There is also disclosed a cannula assembly for providing access to a body cavity which includes an elongate tubular member, an anchor provided on the distal end of the elongate tubular member and an adjustable trocar washer slidably positioned about the elongate tubular member. The adjustable trocar washer includes a compressible collar for securing about the elongate tubular member and a flexible skirt for securing against an incision in skin. A latch mechanism is positioned on the collar to compress the collar about the elongate tubular member. The anchor member is expandable to secure against an interior surface of an abdominal incision.

There is further disclosed a cannula assembly including a valve housing, a cannula member extending distally from the valve housing, an expandable anchor position that the distal end of the cannula member and an adjustable trocar washer slidably mounted along the cannula member. The adjustable trocar washer includes a collar compressible about the tubular member and a flexible skirt formed at the distal end of the collar to seal about the outer surface of an abdominal incision.

DESCRIPTION OF THE DRAWINGS

An exemplary embodiment of the presently disclosed adjustable trocar washer and cannula is disclosed herein with reference to the drawings, wherein.

DETAILED DESCRIPTION

An exemplary embodiment of the presently disclosed adjustable trocar washer will now be described in detail with reference to the drawings wherein like numerals designate identical or corresponding elements in each of the several views. As is common in the art, the term proximal refers to that part or component closer to the user or operator, i.e. surgeon or physician, while the term distal refers to that part or component further away from the user.

Figure 1:
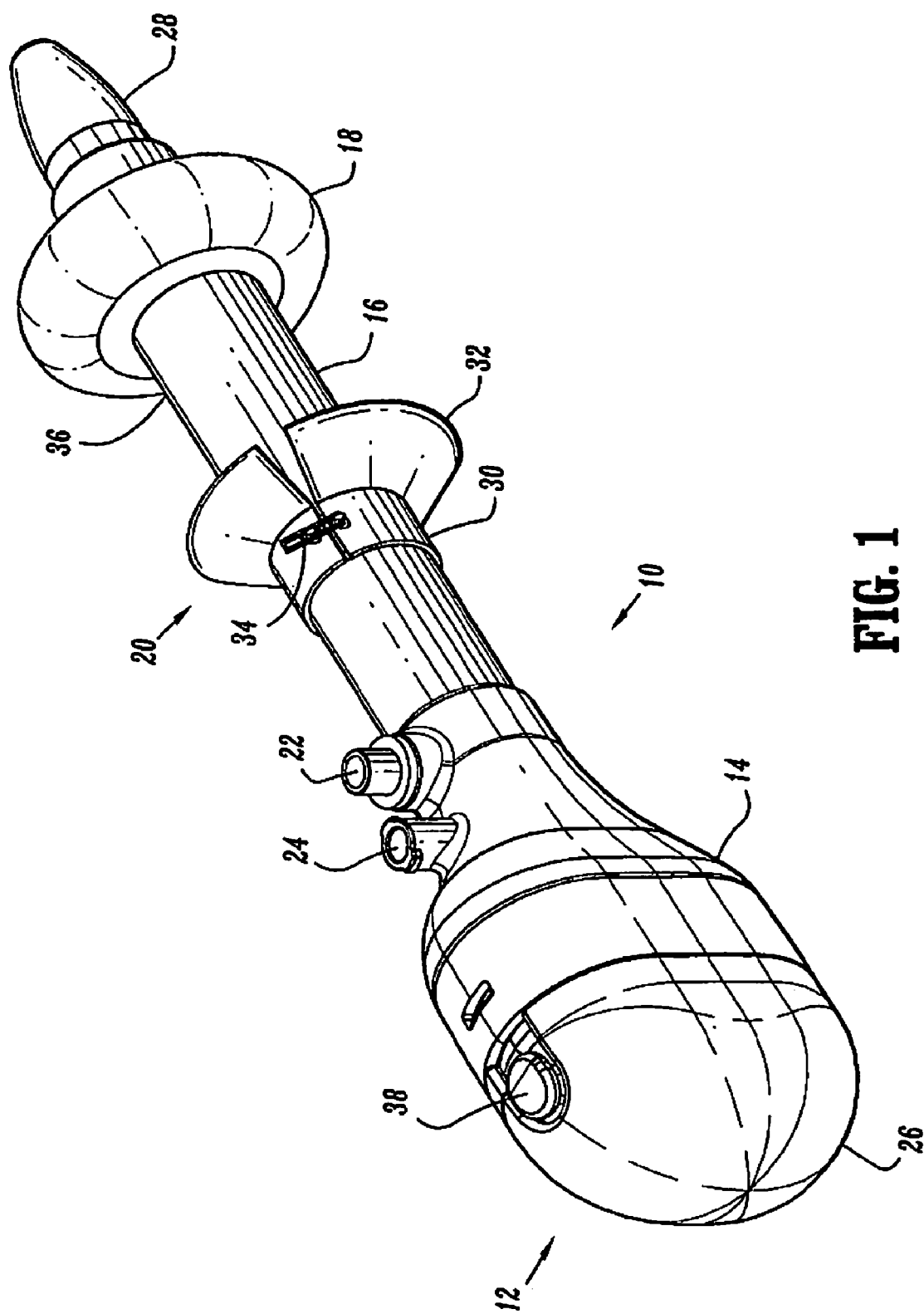
FIG. 1 is a perspective view of a cannula assembly and an adjustable trocar washer positioned about the cannula assembly.

Referring initially to FIG. 1, there is illustrated a surgical instrument including a cannula assembly 10 and an obturator assembly 12 for use in providing an access port into a body cavity. Cannula assembly 10 generally includes a cannula housing 14 and an elongate tubular member 16 extending distally from cannula housing 14. An anchor member 18 is provided on a distal end of elongate tubular member 16 to secure cannula assembly 10 against an inner surface of an abdominal wall. Adjustable trocar washer 20 is movably mounted along elongate member 16 to secure cannula assembly 10 against an outer surface of an abdominal wall. Cannula housing 14 includes an anchor inflation port 22 which is in fluid communication with anchor member 18. Cannula housing 14 additionally includes an insufflation port 24 for providing insufflation fluid into the body cavity.

Obturator assembly 12 includes an obturator housing 26 and an obturator 28 extending distally from obturator housing 26. Obturator assembly 12 facilitates entry of cannula assembly 10 through an incision in the patient's abdominal wall.

Trocar washer 20 is provided to seal an incision in the patient's abdominal wall and stabilize cannula assembly 10 relative to the abdominal wall. Trocar washer 20 includes a compressible collar 30 and a skirt 32 formed at a distal end of compressible collar 30. The collar 30 and skirt 32 may be formed integrally or as separate units attached together. Skirt 32 is formed of a flexible material which is sufficient to seal about the incision in the abdominal wall. Desirably, the skirt 32 has a flared shape. Desirably, the skirt 32 and collar 30 are integrally formed from a resilient material. In one embodiment, at least the skirt 32 is formed of the thermoplastic elastomer (TPE) commercially available under the tradename SANTOPRENE® from Advanced Elastomer Systems, L.P., Akron, Ohio. A compression member or latch mechanism 34 is provided on compressible collar 30 to radially compress the collar 30 and skirt 32 and to secure trocar washer 20 against elongate tubular member 16. As shown, anchor member 18 is provided at a distal end 36 of the elongate tubular member 16. Latches 38 are provided on obturator housing 26 to secure obturator housing 26 relative to cannula housing 14 during insertion of the surgical instrument through an abdominal incision.

Figure 2:
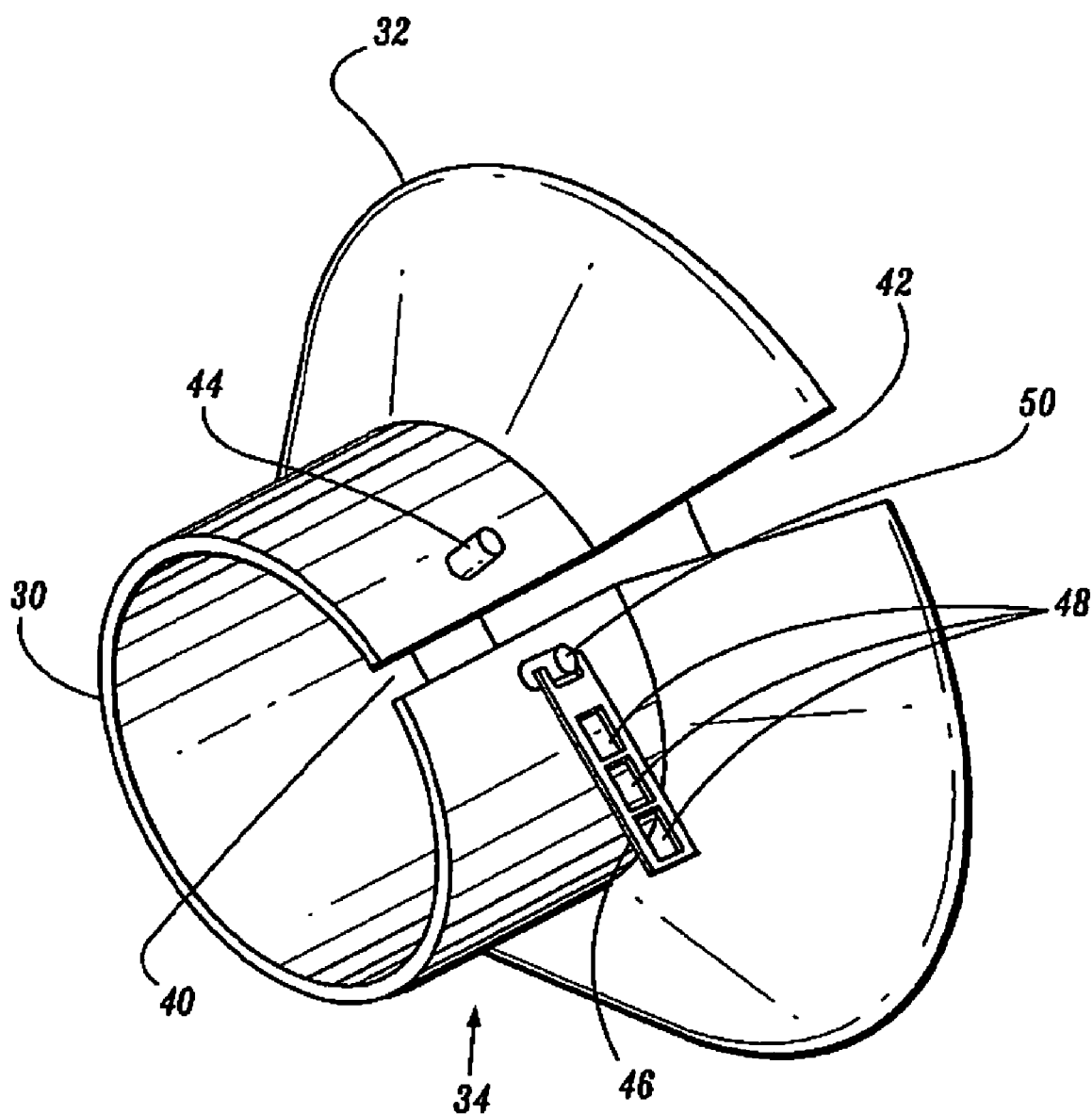
FIG. 2 is a perspective view of the presently disclosed adjustable trocar washer.
Figure 3:
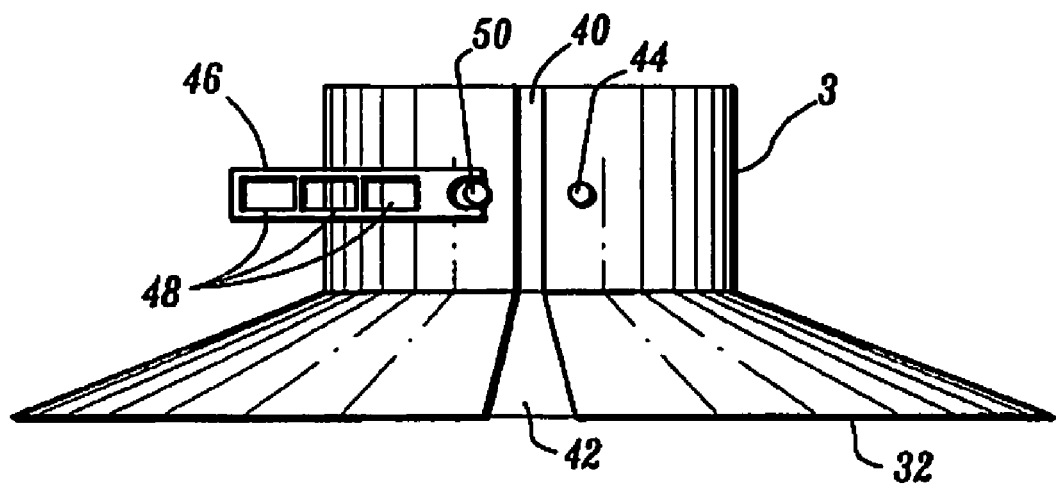
FIG. 3 is a side elevational view of the adjustable trocar washer.
Figure 4:
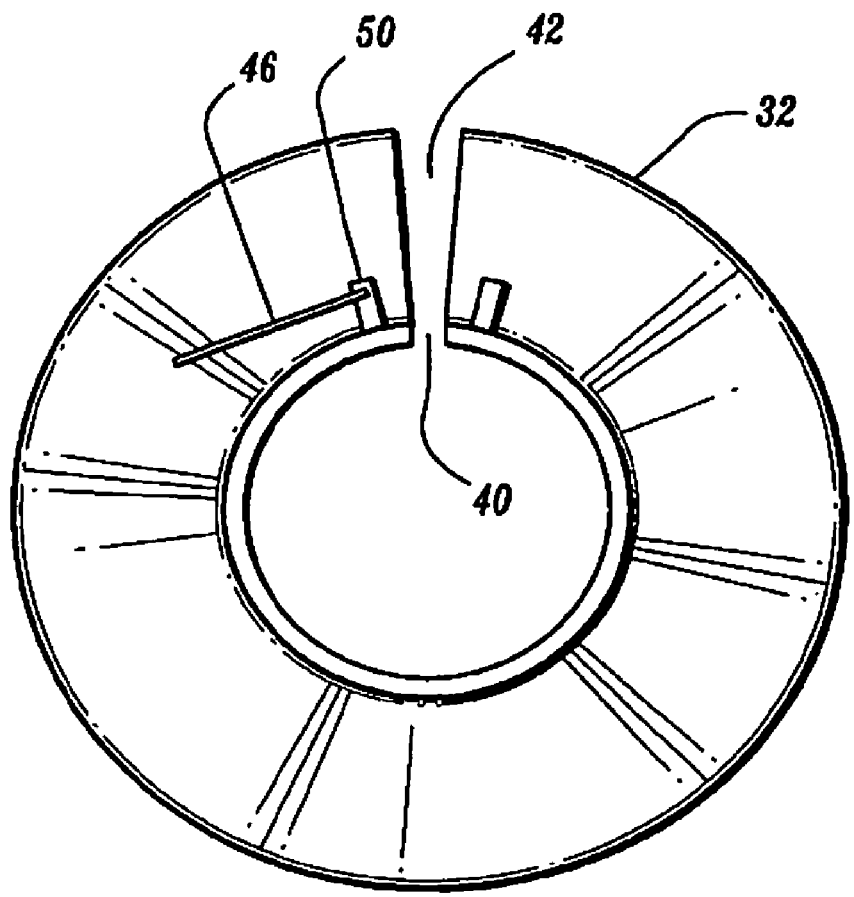
FIG. 4 is a top view of the adjustable trocar washer.

Referring now to FIGS. 2-4, the details of the adjustable trocar washer 20 will now be described. As shown, compressible collar 30 defines a collar slit 40 and skirt 32 defines a skirt slit 42. Collar slit 40 and skirt slit 32 are coextensive to allow trocar washer 20 to be compressed about elongate tubular member 16. Latch mechanism 34 includes a post 44 provided on one side of collar slit 40 and a latch member 46 provided on an opposing side of collar slit 40. Latch member 46 is engageable with post 44 to secure trocar washer 20 about elongate tubular member 16. In one embodiment, latch member 46 is provided with a plurality of latch openings 48 each of which is engageable with post 44 to provide a range of adjustments of compression of trocar washer 20 about elongate tubular member 16.

As shown, latch member 46 is pivotally mounted to a latch post 50 provided on compressible collar 30. Alternatively, latch member 46 may be provided with a "living hinge" type attachment to compressible collar 30.

In a further embodiment, the trocar washer 20 has an over-center clamp. The clamp includes a post on one side of the collar slit 40 and a lever member pivotably attached on the other side of collar slit 40. The lever member is pivotably attached to the post at a location spaced from the first pivotable attachment. The over-center clamp may be arranged as disclosed in certain embodiments of PCT Publication No. WO 02/091307, the disclosure of which is hereby incorporated by reference herein.

Figure 5:
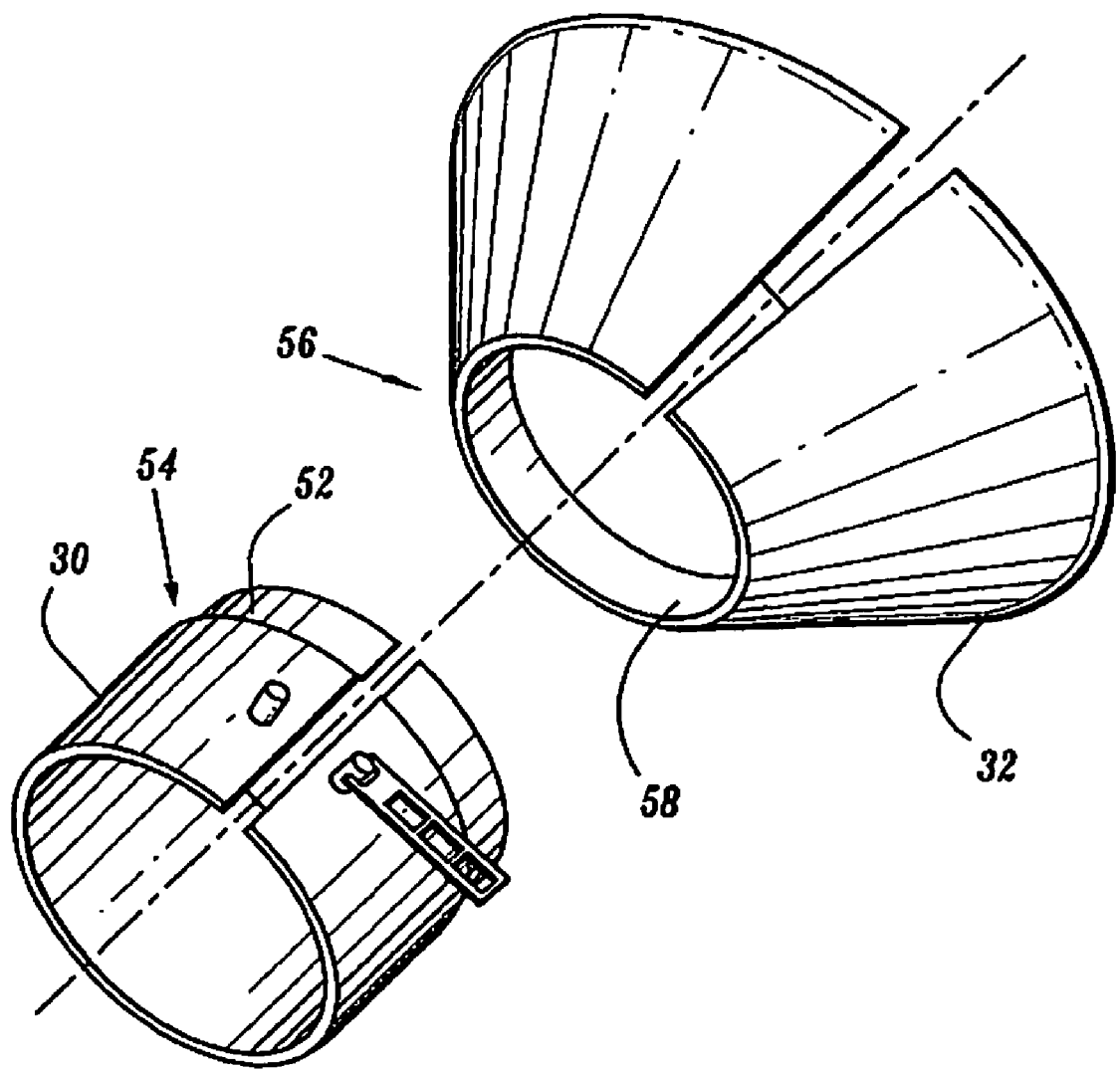
FIG. 5 is a perspective view of the adjustable trocar washer with parts separated.

Referring now to FIG. 5, in order to attach skirt 32 to compressible collar 30, compressible collar 30 is provided with a reduced diameter portion 52 provided at a distal end 54 of compressible collar 30. Skirt 32 is attached to compressible collar 30 by positioning a proximal skirt opening 58, formed at a proximal end 56 of skirt 32, about reduced diameter portion 52 and gluing or otherwise attaching them together. Alternatively, compressible collar 30 may be provided with an enlarged flange at distal end 54 which is configured to be attached to skirt 32. In further embodiments, the collar 30 and skirt 32 are integrally formed.

Figure 6:
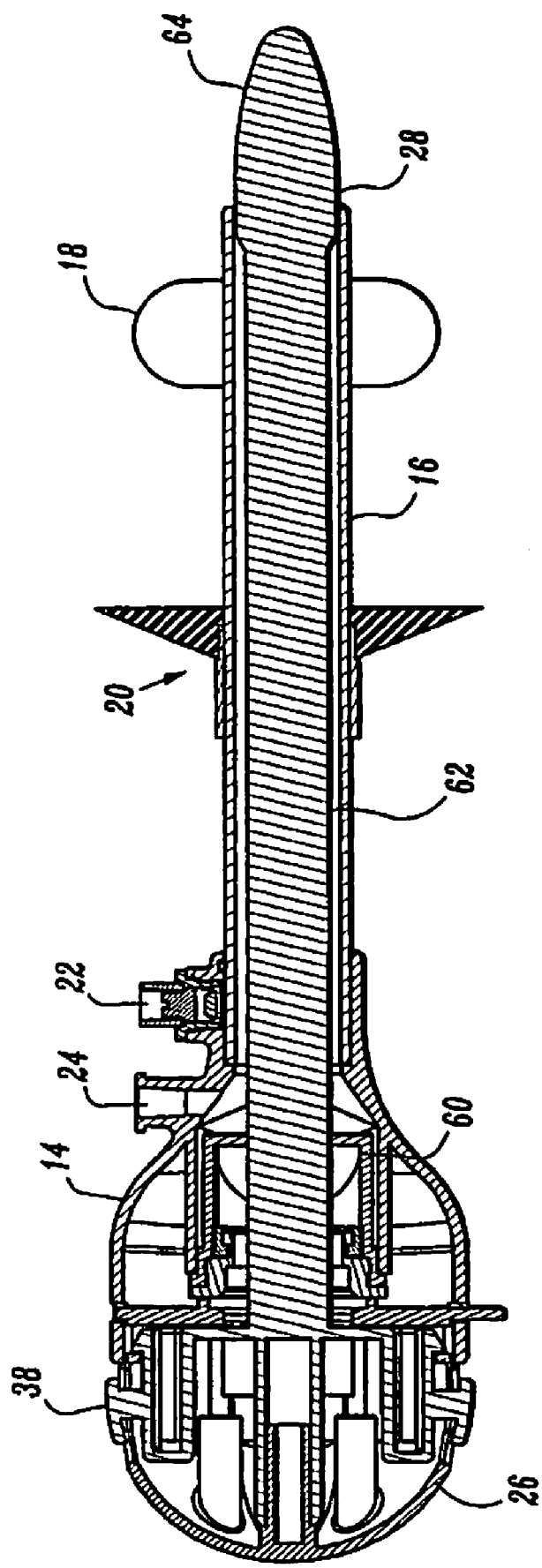
FIG. 6 is a side view, shown in section, of a cannula assembly and the adjustable trocar washer.

Referring now to FIG. 6, cannula housing 14 is provided with a valve assembly 60 to prevent escape of insufflation gases after obturator assembly 12 has been removed. As shown, obturator 28 includes an elongate obturator shaft 62 extending from obturator housing 26. An obturator distal tip 64 is provided at a distal end of obturator shaft 62. Insufflation port 24 is in direct communication with the interior surface of the elongate tubular member 16 to provide insufflation fluids directly into the body. Similarly, anchor inflation port 22 is in fluid communication with anchor member 18 through an inflation channel (not shown) provided in a wall of the elongate tubular member 16. As noted hereinabove, latches 38 are provided to secure obturator housing 26 to cannula housing 14.

Figure 7:
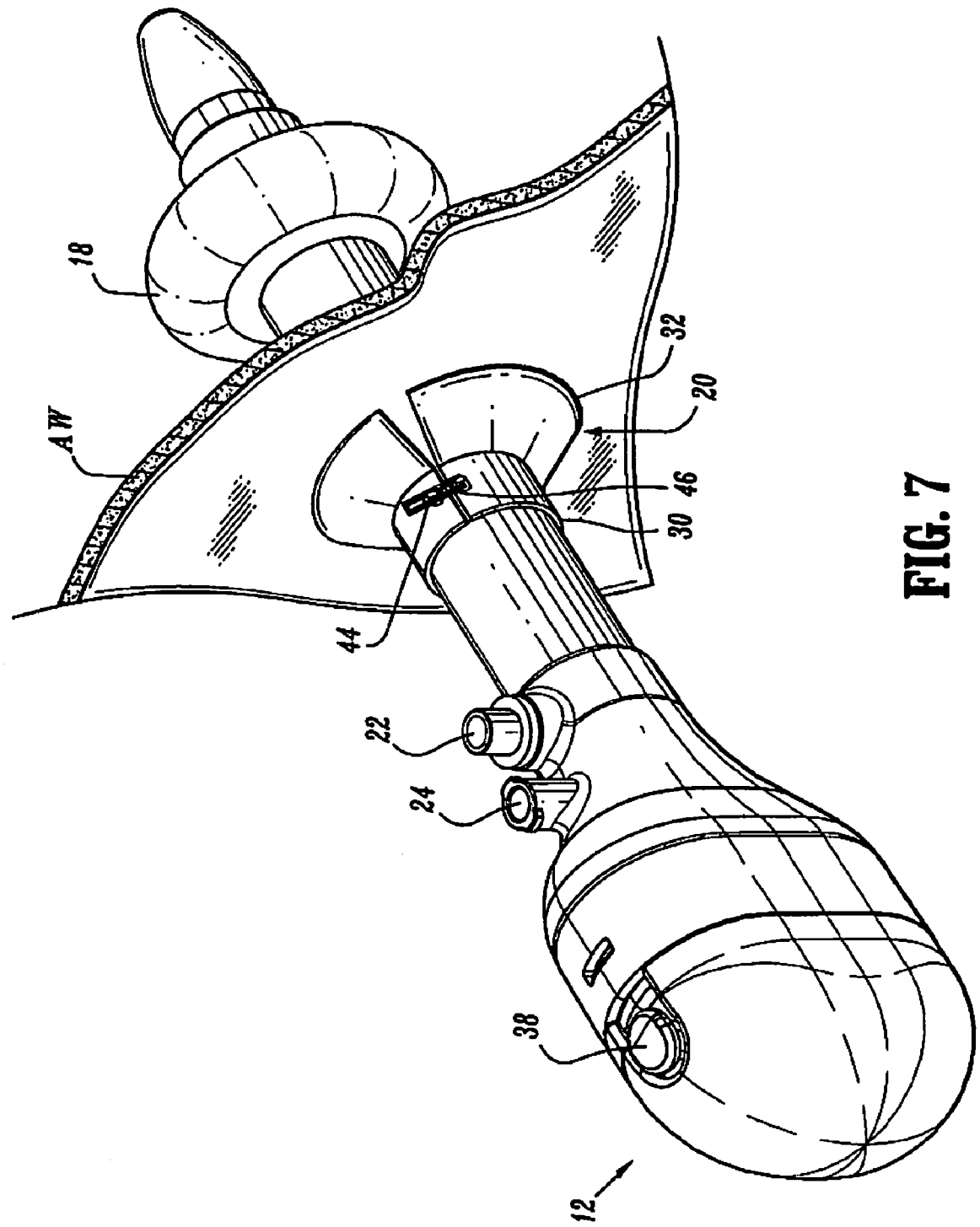
FIG. 7 is a perspective view of the cannula assembly and adjustable trocar washer being secured at an incision in the skin.

Referring now to FIG. 7, the use of the disclosed surgical instrument to provide an access port into an abdominal cavity will now be described. Initially, an incision is made in the abdominal wall. The surgical instrument, with cannula assembly 10 attached to obturator assembly 12, is advanced through the incision until anchor member 18 is located within an internal cavity of the abdominal wall. Thereafter, inflation fluid is provided to inflation port 24 to inflate anchor member 18. Once anchor member 18 has been inflated, the surgical instrument can be drawn proximally to cause inflated anchor member 18 to abut an inner surface of the abdominal wall. Thereafter, trocar washer 20 is slid distally along elongate tubular member 16 until skirt 32 engages the outer surface of the abdominal wall (AW). Once the proper pressure of skirt 32 against abdominal wall (AW) has been achieved, latch member 46 can be pivoted to engage the appropriate latch opening 38 formed in latch member 46 with post 44.

Once the abdominal wall has been secured between anchor balloon 18 and trocar washer 20, obturator assembly 12 can be removed by depressing latches 38 and drawing obturator assembly 12 proximally out of cannula assembly 10. At this point, insufflation fluids can be provided to insufflation port 24 to inflate the cavity within the abdominal wall. The valve assembly 60 provided within cannula housing 14 prevents any escape of insufflation gases and allows for insertion of surgical instruments through cannula assembly 10.

Once the surgical procedure has been completed, the surgical instrument can be withdrawn through cannula assembly 10 and cannula assembly 10 can be removed through the abdominal incision. First, insufflation gasses are released from the body cavity through insufflation port 24. Then anchor member 18 is deflated by removing the inflation fluid from anchor member 18 through inflation port 22. The cannula assembly 10 is removed from the incision after the anchor balloon 18 is deflated.

It will be understood that various modifications may be made to the embodiments disclosed herein. For example, the skirt may be formed of a material which has a medium degree of flexibility such that these skirt provides a vertical support to a the cannula assembly and thus stabilizing the cannula assembly against falling over against the abdominal wall during surgical procedures. Further, alternative latch mechanisms may be provided to secure the compressible collar against the elongate tubular member. Additionally, the disclosed adjustable trocar washer can be used with other devices then a cannula is, such as, for example, a catheter, to secure a tubular member against an outer surface of a patient's skin. Therefore, the above description should not be construed as limiting, but merely as exemplifications of particular embodiments. Those skilled in the art will envision other modifications within the scope and spirit of the claims appended hereto.

The invention claimed is:

1. An adjustable trocar washer for use with a cannula assembly having an elongate tubular member comprising:
a collar including an outer wall defining an internal opening for accommodating an elongate tubular member, the collar being split along at least a portion of a longitudinal length of the outer wall, to thereby permit the collar to move between at least a first condition where the outer wall defines the internal opening having a first internal dimension and at least a second condition where the outer wall defines the internal opening having a second internal dimension different from the first internal dimension;

a skirt connected to the collar, the skirt extending radially and longitudinally relative to the longitudinal axis of the collar, the skirt dimensioned for being positioned against body tissue; and a latch member pivotally mounted to the collar, the latch member being selectively and releasably lockable relative to the collar between at least first and second secured positions to respectively releasably secure the collar in the first condition or the second condition thereof whereby the collar engages the elongate tubular member in secured relation.

2. The adjustable trocar washer as recited in claim 1, wherein the collar is configured to be compressed about the elongate tubular member.

3. The adjustable trocar washer as recited in claim 2, including a post on one side of the slit in the collar and the latch member being on the opposing side of the slit in the collar, the latch member engageable with the post to selectively secure the latch member relative to the collar in either the first and second secured positions of the latch member.

4. The adjustable trocar washer as recited in claim 3, wherein the latch member includes first and second openings positionable over the post to secure the collar about the elongate tubular member, the first and second openings corresponding to respective first and second secured positions of the latch member.

5. The adjustable trocar washer as recited in claim 1, wherein the skirt has sufficient flexibility to seal about an incision in the skin.

6. The adjustable trocar washer as recited in claim 5, wherein the skirt comprises a thermoplastic elastomer (TPE).

7. The adjustable trocar washer as recited in claim 1, wherein the collar has a reduced diameter portion at its distal end and the skirt is secured to the collar at the reduced diameter portion.

8. The adjustable trocar washer as recited in claim 1, wherein the collar comprises an elastomeric material.

9. The adjustable trocar washer as recited in claim 1, wherein the latch member is selectively and releasably lockable relative to the collar between the first, the second and a third secured position of the latch member to respectively releasably secure the collar in the first condition, the second condition or a third condition thereof, whereby in the third condition the outer wall defines the internal opening having a third internal dimension different from the first and second internal dimensions.

10. The adjustable trocar washer as recited in claim 9, further comprising a post on one side of the slit in the collar and the latch member on the opposing side of the slit in the collar, the latch member includes first, second and third openings positionable over the post to secure the collar about the elongate tubular member, the first, second and third openings corresponding to respective first, second and third secured positions of the latch member.

11. A cannula assembly for providing access to a body cavity comprising:

an elongate tubular member defining a longitudinal axis and having proximal and distal ends, the elongate member being dimensioned for introduction through body tissue;

an anchor member disposed on the distal end of the elongate tubular member, the anchor member dimensioned for engagement of one side of the body tissue;

an adjustable trocar washer slidably positioned about the elongate tubular member proximal of the anchor member, the adjustable trocar washer defining a longitudinal axis and having an internal dimension, the adjustable trocar washer being split to permit selective increasing or decreasing of the size of the internal dimension; and a latch member pivotally mounted to the adjustable trocar washer, the latch member being selectively lockable relative to the adjustable trocar washer to secure the adjustable trocar washer in a plurality of positions corresponding to respective different size internal dimensions of the trocar washer to secure the trocar washer about the elongate member, the latch member being releasable from any of the plurality of positions to permit repositioning of the adjustable trocar washer relative to the elongate tubular member.

12. The cannula assembly as recited in claim 11, wherein the anchor member is expandable.

13. The cannula assembly as recited in claim 11, wherein the adjustable trocar washer includes a flexible skirt, the skirt dimensioned for engagement of a second side of the body tissue.

14. The cannula assembly as recited in claim 13, wherein the adjustable trocar washer includes a general longitudinal slit along the longitudinal length thereof.

15. The cannula assembly as recited in claim 14, further comprising a post engageable with the latch member.

16. The cannula assembly as recited in claim 15, wherein the post is positioned on one side of the slit and the latch member is positioned on an opposite side of the slit.

17. The cannula assembly as recited in claim 16, wherein the latch member includes first and second openings for reception of the post, the first and second openings corresponding to a different size internal dimensions of the trocar washer.

18. The adjustable trocar washer as recited in claim 17, wherein the latch member includes first, second and third openings positionable over the post to secure the collar about the elongate tubular member, the first, second and third openings corresponding to respective first, second and third secured positions of the latch member.

* * * * *